United States Patent
Gipson

(10) Patent No.: US 10,668,203 B2
(45) Date of Patent: *Jun. 2, 2020

(54) SYSTEM AND METHOD FOR CARDIOPULMONARY BYPASS USING HYPOBARIC OXYGENATION

(71) Applicant: Keith Gipson, Wallingford, CT (US)

(72) Inventor: Keith Gipson, Wallingford, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 16/412,820

(22) Filed: May 15, 2019

(65) Prior Publication Data
US 2019/0275227 A1    Sep. 12, 2019

Related U.S. Application Data

(63) Continuation of application No. 15/024,070, filed as application No. PCT/US2014/056722 on Sep. 22, 2014, now Pat. No. 10,335,531.
(Continued)

(51) Int. Cl.
*A61M 1/16* (2006.01)
*A61M 1/36* (2006.01)
(Continued)

(52) U.S. Cl.
CPC ............ *A61M 1/1698* (2013.01); *A61M 1/32* (2013.01); *A61M 1/3632* (2014.02);
(Continued)

(58) Field of Classification Search
CPC .... A61M 1/1698; A61M 1/32; A61M 1/3632; A61M 1/3666; A61M 1/3667;
(Continued)

(56) References Cited

U.S. PATENT DOCUMENTS 3,142,296 A   7/1964   Love
3,927,981 A   12/1975  Viannay et al.
(Continued)

FOREIGN PATENT DOCUMENTS

EP   0598424 A2   5/1994
EP   1036567 B1   11/2006
(Continued)

OTHER PUBLICATIONS

Barak, et al., "Microbubbles: Pathophysiology and Clinical Implications," Chest, vol. 128, No. 4, Oct. 2005, pp. 2918-2932.
(Continued)

*Primary Examiner* — John Kim
(74) *Attorney, Agent, or Firm* — Cantor Colburn LLP

(57) ABSTRACT

A system for cardiopulmonary bypass, including: a cardiopulmonary bypass reservoir configured to store a blood; a pump in fluid communication with the cardiopulmonary bypass reservoir configured to provide pressure to the system; an oxygen source including a pressure regulator configured to regulate an oxygen pressure; an oxygenator fluidly connected to the pressure regulator of the oxygen source via an sweep gas inlet, wherein the sweep gas inlet is configured to have a subatmospheric pressure and the oxygenator is configured to oxygenate the blood; a vacuum regulator fluidly connected to the oxygenator via an sweep gas outlet, and configured to provide the subatmospheric pressure; a flow restrictor fluidly connected to the sweep gas inlet and configured to allow for a pressure drop from the oxygen source to the oxygenator; and an arterial filter fluidly connected to a blood outlet of the oxygenator and to the cardiopulmonary bypass reservoir.

21 Claims, 9 Drawing Sheets

Related U.S. Application Data

(60) Provisional application No. 61/881,684, filed on Sep. 24, 2013.

(51) Int. Cl.
  *A61M 1/32* (2006.01)
  *A61M 39/24* (2006.01)

(52) U.S. Cl.
  CPC ........ *A61M 1/3666* (2013.01); *A61M 1/3667* (2014.02); *A61M 39/24* (2013.01); *A61M 2202/0208* (2013.01); *A61M 2205/3375* (2013.01); *A61M 2205/502* (2013.01)

(58) Field of Classification Search
  CPC .......... A61M 39/24; A61M 2205/3375; A61M 2205/502; A61M 2202/0208
  See application file for complete search history.

(56) References Cited

U.S. PATENT DOCUMENTS

| | | |
|---|---|---|
| 4,108,607 A | 8/1978 | Pearson et al. |
| 5,055,198 A | 10/1991 | Shettigar |
| 5,110,548 A | 5/1992 | Montevecchi |
| 5,158,534 A | 10/1992 | Berry et al. |
| 5,362,406 A | 11/1994 | Gsell |
| 5,382,407 A | 1/1995 | Leonard |
| 5,425,803 A | 6/1995 | van Schravendijk et al. |
| 5,591,399 A | 1/1997 | Goldman et al. |
| 5,645,625 A | 7/1997 | van Schravendijk et al. |
| 5,772,736 A | 6/1998 | van Schravendijk et al. |
| 6,267,926 B1 | 7/2001 | Reed et al. |
| 6,328,789 B1 | 12/2001 | Spranger |
| 6,478,962 B1 | 11/2002 | Brockhoff et al. |
| 6,524,267 B1 | 2/2003 | Gremel et al. |
| 6,572,821 B2 | 6/2003 | Knott |
| 6,582,387 B2 | 6/2003 | Derek et al. |
| 6,596,058 B2 | 7/2003 | Gerner et al. |
| 6,726,651 B1 | 4/2004 | Robinson et al. |
| 7,740,800 B2 | 6/2010 | Olsen et al. |
| 2003/0205831 A1 | 11/2003 | Rawlins et al. |
| 2005/0192525 A1 | 9/2005 | Wieting et al. |
| 2009/0230058 A1 | 9/2009 | Boris-Moeller |
| 2010/0101657 A1 | 4/2010 | Morley et al. |
| 2010/0274170 A1 | 10/2010 | Carpenter et al. |
| 2010/0331767 A1 | 12/2010 | Frankowski et al. |
| 2011/0245750 A1 | 10/2011 | Lynch et al. |

FOREIGN PATENT DOCUMENTS

| | | | |
|---|---|---|---|
| JP | 2001346871 A | 12/2001 | |
| JP | 2012501797 A | 1/2012 | |
| JP | 2013509238 A | 3/2013 | |
| WO | 02100510 A1 | 12/2002 | |

OTHER PUBLICATIONS

Behnke, et al., "The Rate of Elimination of Dissolved Nitrogen in Man in Relation to the Fat and Water Content of the Body," American Journal of Physiology, Nov. 30, 1935, vol. 114, pp. 137-146.

Brooker, et al., "Cardiotomy Suction: A Major Source of Brain Lipid Emboli During Cardiopulmonary Bypass," Annals of Thoracic Surgery, vol. 65, Issue 6, Jun. 1998, pp. 1651-1655.

Curry, et al., "Negative Pressure Breathing Enhances Nitrogen Elimination," Aviation, Space and Environmental Medicine, vol. 74, No. 10, Oct. 2003, pp. 1034-1039.

Duncan, et al., "Test of the Epstein-Plesset Model for Gas Microparticle Dissolution in Aqueous Media: Effect of Surface Tension and Gas Undersaturation in Solution," Langmuir, vol. 20, No. 7, Mar. 2004, pp. 2567-2578.

Eger, II, et al., "Minimum Alveolar Concentration of I-653 and Isoflurane in Pigs: Definition of a Supramaximal Stimulus," Anesthesia & Analgesia, vol. 67, No. 12, Dec. 1988, pp. 1174-1176.

Farhi, et al., "Determination of disssolved N2 in blood by gas chromatography and (a-A)N2 difference," Journal of Applied Physiology, Jan. 1, 1963, vol. 18, No. 1, pp. 97-106.

Grocott, et al., "Cognitive Dysfunction After Cardiac Surgery: Revisiting Etiology," Seminars in Cardiothoracic and Vascular Anesthesia, vol. 9, No. 2 (Jun.), 2005, ppl 123-129.

High, et al., "Principles of Oxygenator Function: Gas Exchange, Heat Transfer, and Operation," in Cardiopulmonary Bypass Principles and Practice, 2nd Ed, Chap. 4, 2000, pp. 49-65, Philadelphia, PA, Lippincott, Williams & Wilkins.

International Preliminary Report on Patentability for International Application No. PCT/US2014/56722, international filing date of Sep. 22, 2014, dated Mar. 29, 2016, 8 pages.

International Search Report for International Application No. PCT/US2014/034991, international filed of Apr. 22, 2014, dated Aug. 28, 2014, 8 pages.

James, et al., "Anesthetic Considerations at Moderate Altitude," Anesthesia & Analgesia, vol. 63, No. 12, Dec. 1984, pp. 1097-1105.

Kurusz, et al., "Bubbles and bypass: an update," Perfusion, Feb. 2004, 19, Suppl. 1, pp. S49-S55.

Lynch, et al., "Gaseous Microemboli Sizing in Extracorporeal Circuits Using Ultrasound Backscatter," Ultrasound in Medicine and Biology, vol. 33, No. 10, Oct. 2007, pp. 1661-1675.

Lynch, et al., "Monitoring Microemboli During Cardiopulmonary Bypass with the EDAC Quantifier," JECT, Sep. 2010, vol. 42(3), pp. 212-218.

Newman, et al., "Central nervous system injury associated with cardiac surgery," Lancet, vol. 368, Aug. 19, 2006, pp. 694-703.

Potger, et al., "Microbubble Transmission during Cardiotomy Infusion of a Hardshell Venous Reservoir with Integrated Cardiotomy versus a Softshell Venous Reservoir with Separated Cardiotomy: An In Vitro Comparison," JECT, Jun. 2013, vol. 45(2), pp. 77-85.

Rudolph, et al., "Use of a large bore syringe creates significantly fewer high intensity transient signals (HITS) into a cardiopulmonary bypass system than a small bore syringe," Perfusion, Jan. 2006, 21(1), pp. 67-71.

Wang, et al., "Clinical Real-Time Monitoring of Gaseous Microemboli in Pediatric Cardiopulmonary Bypass," Artificial Organs, vol. 33, No. 11, 2009, pp. 1026-1030.

Written Opinion for International Application No. PCT/US2014/56722, international filed of Sep. 22, 2014, dated Jan. 16, 2015, 7 pages.

SYSTEM AND METHOD FOR CARDIOPULMONARY BYPASS USING HYPOBARIC OXYGENATION

CROSS-REFERENCE TO RELATED APPLICATIONS

This application is a Continuation of U.S. Nonprovisional patent application Ser. No. 15/024,070, filed 23 Mar. 2016, and issued as U.S. Pat. No. 10,335,531, which is the U.S. national stage application of International Application No. PCT/US2014/056722, which has an international filing date of 22 Sep. 2014, and which claims priority to U.S. Provisional Patent Application No. 61/881,684, filed 24 Sep. 2013, the contents of each of which are incorporated herein by reference in their entirety.

FIELD

The disclosure relates generally to a system and method for cardiopulmonary bypass, and more particularly to a system and method for cardiopulmonary bypass using hypobaric oxygenation to eliminate gaseous microemboli.

BACKGROUND

Primarily during heart operations there is a transient need to replace the function of the heart and lungs by artificial means. Also in more chronic disease states as e.g. during severe pulmonary, cardiac, or renal failure, maintenance of life can be upheld by different artificial means until an organ for transplantation becomes available. In many clinical situations there is a need for an extracorporeal circuit wherein the artificial organ is incorporated.

The contact of blood on surfaces made out of foreign material inevitably initiates blood coagulation and the formation of clots. This is controlled by the use of anticoagulant drugs. Also gas bubbles are easily formed in blood, which is propelled into the circulation of a living being during extracorporeal circulation. This phenomenon is due to cavitation, temperature gradients, and differences in the amount of gases dissolved between own and incoming blood. In the case of heart surgery the extracorporeal circuit contains a gas-exchange device i.e. an oxygenator, which is used not only for oxygenation but also for the disposal of carbon dioxide. The close contact between blood and gas in the oxygenator poses even higher risks for inadvertent entry of gas bubbles into the circulating blood.

At present, to avoid bubble formation during heart surgery membrane-type oxygenators are used instead of bubble-oxygenators, high temperature gradients are avoided, and use of suction in the operating field is controlled. Heart-lung machines contain an air bubble sensor that warns the perfusionist, i.e. the person maneuvering the heart-lung machine, of the appearance of small bubbles and immediately stops the main pump when larger bubbles appear. Typically, the bubble sensor can discern bubbles with a diameter of approximately 0.3 mm, and stops the main pump when a bubble with a diameter of 3-5 mm is recognized.

Cardiac surgery is frequently complicated by postoperative neurocognitive deficits that degrade functional capacity and quality of life while increasing healthcare costs. Multifactorial contributors to this significant public health problem likely include gaseous microemboli (GME). The arterial circulation receives thousands of 10-40 µm GME during cardiopulmonary bypass (CPB) despite the use of membrane oxygenation and arterial filtration. Vasoocclusive GME cause tissue ischemia and denude endothelium in the brain and other end organs, leading to vascular dilation, increased permeability, activation of platelets and clotting cascades, and recruitment of complement and cellular mediators of inflammation.

There are numerous technical solutions in the prior art to separate already formed bubbles from circulation. Current perfusion practice generally targets mildly hyperoxic blood gases during CPB. This target is achieved by lowering the partial pressure of oxygen in oxygenator sweep gas by dilution with air, thereby engendering the needless side effect of dissolving nitrogen in blood. The blood, thus saturated with dissolved gas, is poorly able to dissolve gases that exist in bubble form as GME.

However, there is also a need to diminish the generation of gas bubbles, i.e. the formation of gas bubbles during heart surgery, for example. In a blood bubble, in the liquid-gas interface, there is an approximately 40-100 Å (i.e. 4-10 nanometer) deep layer of lipoproteins that denaturate due to direct contact with the foreign material, e.g. gas. In turn, the Hageman factor is activated which initiates coagulation and the concomitant adverse consumption of factors promoting coagulation, which in the post-pump period are desperately needed to prevent bleeding from the surgical wound.

Accordingly, a system and method capable of inhibiting the bubble formation in the blood in the absence of nitrogen during extracorporeal circulation would be desirable.

SUMMARY

Disclosed is a method and apparatus of hypobaric oxygenation to lower the pressure of pure oxygen sweep gas without dilution, thus achieving mildly hyperoxic blood gases in the absence of nitrogen. This approach lowered the sum of partial pressures of dissolved gases to subatmospheric levels, thereby creating a powerful gradient for reabsorption of GME into the aqueous phase. Both in vitro and in vivo approaches are utilized to characterize the elimination of GME from CPB circuits using hypobaric oxygenation, which was accompanied by a reduction in dilated brain capillaries in swine.

In an embodiment, a system for cardiopulmonary bypass, including: a cardiopulmonary bypass reservoir configured to store a blood; a pump in fluid communication with the cardiopulmonary bypass reservoir configured to provide pressure to the system; an oxygen source including a pressure regulator configured to regulate an oxygen pressure; an oxygenator fluidly connected to the pressure regulator of the oxygen source via an sweep gas inlet, wherein the sweep gas inlet is configured to have a subatmospheric pressure and the oxygenator is configured to oxygenate the blood; a vacuum regulator fluidly connected to the oxygenator via an sweep gas outlet, and configured to provide the subatmospheric pressure; a flow restrictor fluidly connected to the sweep gas inlet and configured to allow for a pressure drop from the oxygen source to the oxygenator; and an arterial filter fluidly connected to a blood outlet of the oxygenator and to the cardiopulmonary bypass reservoir.

A system for cardiopulmonary bypass, including: an oxygen source including a pressure regulator configured to regulate an oxygen pressure; an oxygenator fluidly connected to the pressure regulator of the oxygen source via an sweep gas inlet, wherein the sweep gas inlet is configured to have a subatmospheric pressure and the oxygenator is configured to oxygenate a blood; a vacuum regulator fluidly connected to the oxygenator via an sweep gas outlet and configured to provide the subatmospheric pressure; and a flow restrictor fluidly connected to the sweep gas inlet and configured to allow for a pressure drop from the oxygen source to the oxygenator.

A system for cardiopulmonary bypass, including: a cardiopulmonary bypass reservoir; a pump in fluid communication with the cardiopulmonary bypass reservoir configured to provide pressure to the system; an oxygen source including a pressure regulator configured to regulate an oxygen pressure; an oxygenator fluidly connected to the pressure regulator of the oxygen source via an sweep gas inlet, wherein the sweep gas inlet is configured to have a subatmospheric pressure and the oxygenator is configured to oxygenate blood; a vacuum regulator fluidly connected to the oxygenator via an sweep gas outlet, and configured to provide the subatmospheric pressure; a flow restrictor fluidly connected to the sweep gas inlet and configured to allow for a pressure drop from the oxygen source to the oxygenator; an arterial filter fluidly connected to a blood outlet of the oxygenator configured to filter the blood; and a patient interface fluidly connected to the arterial filter and to the cardiopulmonary bypass reservoir.

A system for cardiopulmonary bypass, including: an oxygen source including a pressure regulator configured to regulate an oxygen pressure; an air source; a flow control configured to receive the oxygen source and the air source; a vaporizer in fluid communication with the flow control; a sweep gas reservoir in fluid communication with the vaporizer; an oxygenator fluidly connected to a pressure regulator of the sweep gas reservoir via an sweep gas inlet, wherein the sweep gas inlet is configured to have a subatmospheric pressure and the oxygenator is configured oxygenate a blood; a vacuum regulator fluidly connected to the oxygenator via an sweep gas outlet, and configured to provide the subatmospheric pressure; and a flow restrictor fluidly connected to the sweep gas inlet and configured to allow for a pressure drop from the oxygen source to the oxygenator.

A method for cardiopulmonary bypass, the method including: providing a subatmospheric pressure in an oxygenator via a vacuum regulator; introducing subatmospheric pressure oxygen to the oxygenator via a pressure regulator and a flow restrictor; and introducing blood to be oxygenated to the subatmospheric pressure oxygen.

A system for cardiopulmonary bypass, including: a cardiopulmonary bypass reservoir; a pump in fluid communication with the cardiopulmonary bypass reservoir configured to provide pressure to the system; an oxygen source including a pressure regulator configured to regulate an oxygen pressure; an oxygenator fluidly connected to the pressure regulator of the oxygen source via an sweep gas inlet, and configured to receive blood from the cardiopulmonary bypass reservoir wherein the sweep gas inlet is configured to have a subatmospheric pressure and the oxygenator is configured to oxygenate blood; a patient reservoir in fluid communication with a blood outlet of the oxygenator; a second pump in fluid communication with the patient reservoir configured to additionally provide pressure to the system; and a patient simulator configured to introduce carbon dioxide into the blood and remove oxygen from the blood, wherein the patient simulator is fluidly connected to a cardiopulmonary bypass reservoir.

BRIEF DESCRIPTION OF THE FIGURES

The accompanying drawings incorporated in and forming a part of the specification embodies several aspects of the present disclosure and, together with the description, serves to explain the principles of this disclosure. In the drawings.

DETAILED DESCRIPTION

Figure 1A:
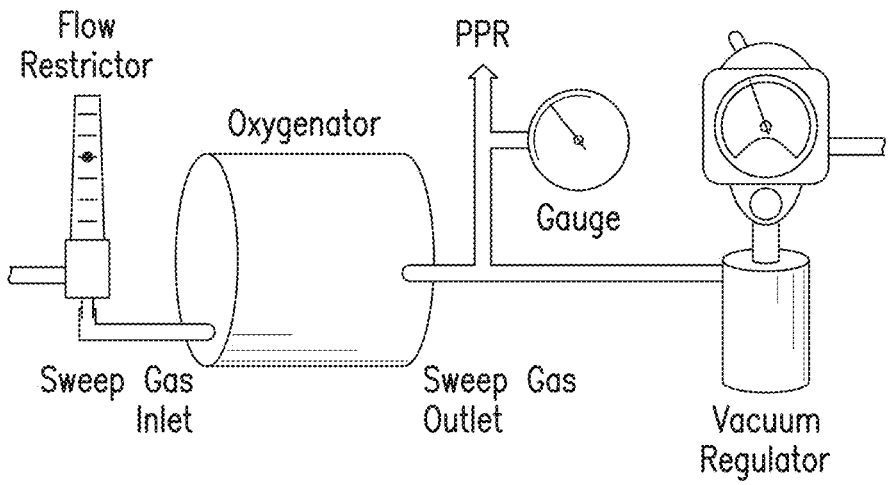
FIG. 1A is a schematic representation of an embodiment of a hypobaric oxygenation apparatus.

The following disclosure will detail particular embodiments, which provides methods and systems for cardiopulmonary bypass. An overview of the mechanism and methods used herein is provided.

Hypobaric oxygenation controls the oxygenator's gas:blood $O_2$ diffusion gradient to achieve desired blood gases without using nitrogen. The resultant decrease in dissolved blood gases favors aqueous reabsorption of GME, resulting in enhanced GME removal observed throughout the CPB circuit. The magnitudes of the observed effects on GME seem consistent with published dynamics of air microparticles in undersaturated aqueous solutions. Of note, blood gas undersaturation is more important than denitrogenation alone. In vitro data demonstrate the difference between a denitrogenated normobaric oxygen control condition and a denitrogenated/undersaturated hypobaric oxygenation condition. An additional physical effect of subatmospheric pressures within the oxygenator's hollow fibers may contribute to oxygenator GME removal, but not to GME removal at more distal sites.

As the beneficial effect of hypobaric oxygenation on GME continues as blood flows into the patient, additional benefits may be realized on air entrained from the surgical field into the arterial circulation during open-heart procedures. Hypobaric oxygenation should also ameliorate concerns about increased GME delivery due to pulsatile flow, centrifugal pump cavitation, and outgassing during vacuum-assisted venous drainage or with rapid temperature changes.

The reduction in brain microvascular injury in animals managed with hypobaric oxygenation suggests improved end-organ function following CPB. While hypobaric oxygenation practically eliminated GME delivery, capillary dilations were only partially reduced. Recycled mediastinal shed blood used to maintain the animals' hematocrit may also increase lipid embolization and may account for residual microvascular damage seen in the hypobaric condition.

Hypobaric oxygenation does not change CPB circuit priming volumes, material composition, or ease of use. The perfusionist controls $PaO_2$ by adjusting the pressure of pure oxygen sweep gas rather than adjusting the sweep gas oxygen content, while $PaCO_2$ is still adjusted by varying the sweep gas flow rate. As partial pressures of anesthetic vapors are also reduced in proportion to the sweep gas pressure, an adjustment of anesthetic concentration will be necessary to ensure adequate anesthesia. As the oxygenator housing must be sealed in order to apply subatmospheric pressures, a suitable pressure relief system must exist to prevent gross air embolism in the event of occlusion of the sweep gas outlet or vacuum failure. Application of overly negative sweep gas pressures could result in hemoglobin desaturation, the solution for which would be to increase the sweep gas pressure or disconnect the vacuum source. Hypobaric oxygenation should be used along with, rather than instead of, arterial filtration in the CPB circuit. Among other benefits, arterial filtration reduces the size of GME, thereby increasing the surface-to-volume ratio and promoting rapid reabsorption under conditions of hypobaric oxygenation.

Reference is now made to the drawings, wherein like reference numerals are used to refer to like elements throughout the disclosure.

FIGS. 1A-1D relate to hypobaric oxygenation in vitro. FIG. 1A refers to a hypobaric oxygenation apparatus. Pure oxygen is supplied to the sweep gas inlet of a standard hollow fiber microporous membrane oxygenator with a sealed housing. Alternatively, the oxygenator may not contain micropores. The housing of the oxygenator may be sealed by physically occluding the vents of a commercially available oxygenator housing, including physically occluding the vents with epoxy putty. Similarly, any suitable method may be used to obtain a sealed housing for the oxygenator. A regulated vacuum source at the sweep gas outlet applies user-determined variable subatmospheric pressure to the sweep gas compartment to regulate the partial pressure gradient for blood oxygenation. A vacuum gauge measures the pressure applied, while a positive-pressure relief valve (PPR) insures against creation of positive pressures. A flowmeter, e.g., a needle-valve flowmeter, at the sweep gas inlet regulates sweep gas flow rate and thus $CO_2$ removal, while allowing a pressure drop from ambient to subatmospheric.

Figure 1B:
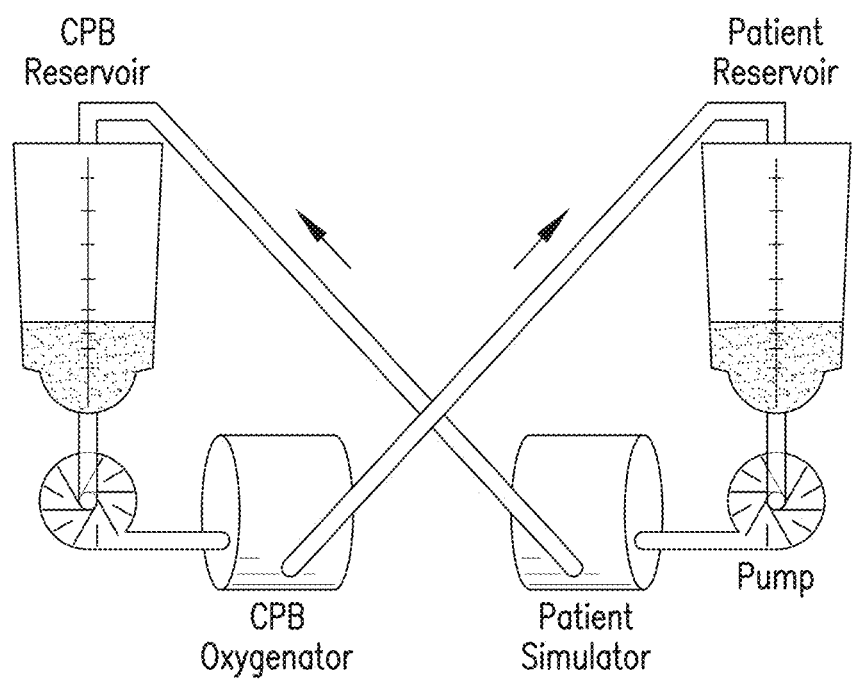
FIG. 1B is a schematic representation of an embodiment of an in vitro gas exchange circuit.

FIG. 1B refers to an in vitro gas exchange circuit. A mixture of human red blood cells (RBCs), fresh frozen plasma (FFP), and minimal crystalloid (Hct~30%) from a CPB reservoir is pumped (3.5 liters/minute) to the CPB oxygenator (37° C.), where oxygenation occurs with pure oxygen sweep gas at variable subatmospheric pressure. The blood then passes into a Patient Simulator consisting of a reservoir, pump, and oxygenator that removes $O_2$ and adds $CO_2$ using pure $CO_2$ sweep gas at very low pressure (1 liter/minute, 0.1 ata). Blood gases were sampled downstream of the CPB oxygenator (arterial) and the Patient Simulator (venous, n=3 samples per condition). The simulated patient produced normal venous blood gas values.

To assess the effect of sweep gas pressure on blood pressure at the oxygenator outlet, paired measurements were performed at sweep gas pressures of ambient, 0.5 atmospheres (ata), and 0.1 ata (n=14 trials per condition). Blood pressure was measured using a pressure transducer (ICU Medical, San Clemente, Calif.) connected to a demodulator (Validyne Corporation, Northridge, Calif.), whose voltage output was calibrated against a water column, digitized (DI-145) and recorded using Windaq software (DATAQ Instruments, Akron, Ohio).

Figure 1C:
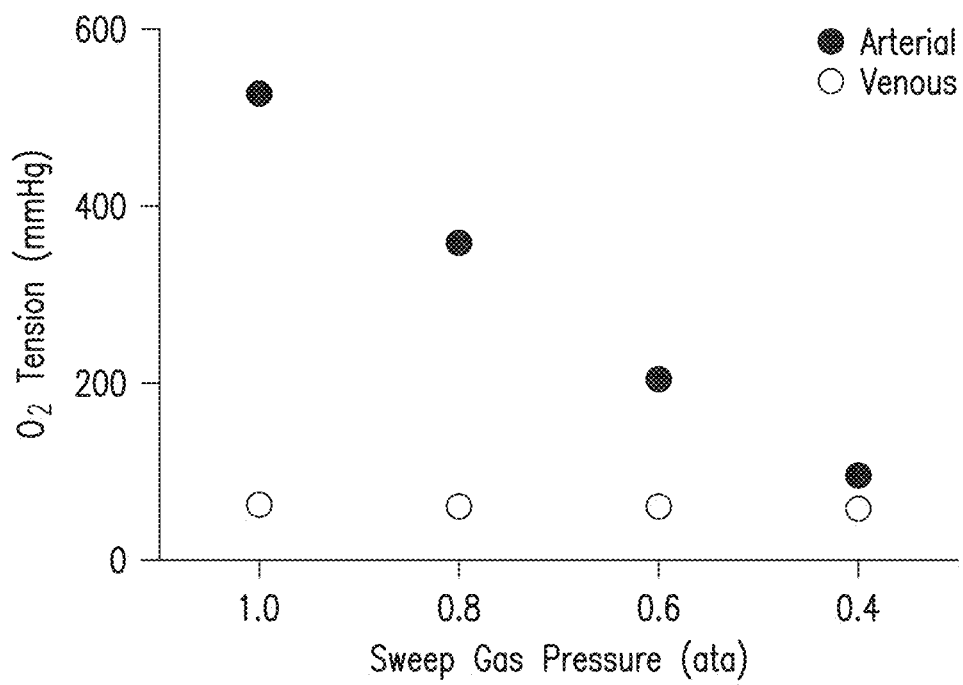
FIG. 1C is a chart of $O_2$ tension (millimeters of mercury, mmHg) versus sweep gas pressure (atmospheres, ata) illustrating the relationship between oxygenation and sweep gas pressure.
Figure 1D:
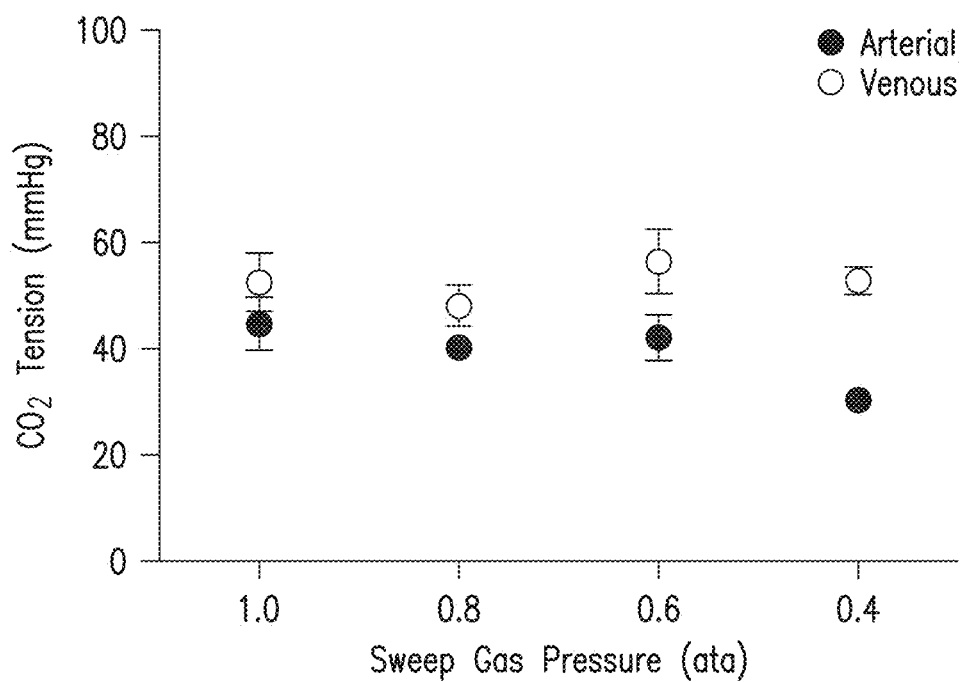
FIG. 1D is a chart of $CO_2$ tension (millimeters of mercury, mmHg) versus sweep gas pressure (total ambient pressure, ata) illustrating the relationship between carbon dioxide removal and sweep gas pressure.

FIGS. 1C and 1D illustrate that the application of subatmospheric sweep gas pressure in the CPB oxygenator reduced arterial oxygenation in the expected linear manner independent of $CO_2$ removal.

Figure 2A:
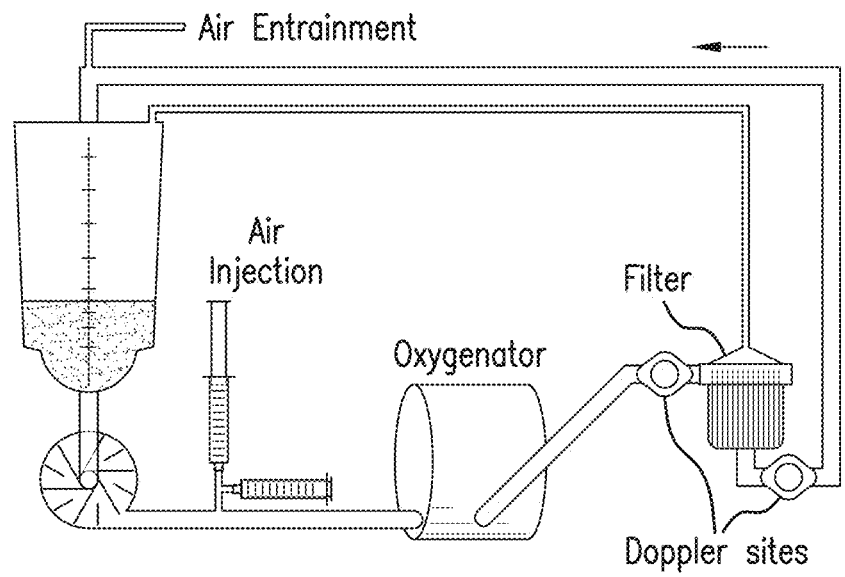
FIG. 2A is a schematic representation of an embodiment of a single oxygenator CPB circuit configuration.

FIGS. 2A-2D further relate to hypobaric oxygenation in vitro. Specifically, hypobaric oxygenation greatly enhances GME removal in vitro. FIG. 2A illustrates a single oxygenator CPB circuit configuration with arterial filter and purge line returning to reservoir. Locations of air introduction and Doppler GME monitoring are shown. Arrow indicates direction of blood flow (5 liters/minute, 37° C.). The Doppler signal was processed via custom analog envelope detector then digitized and recorded as above.

Figure 2B:
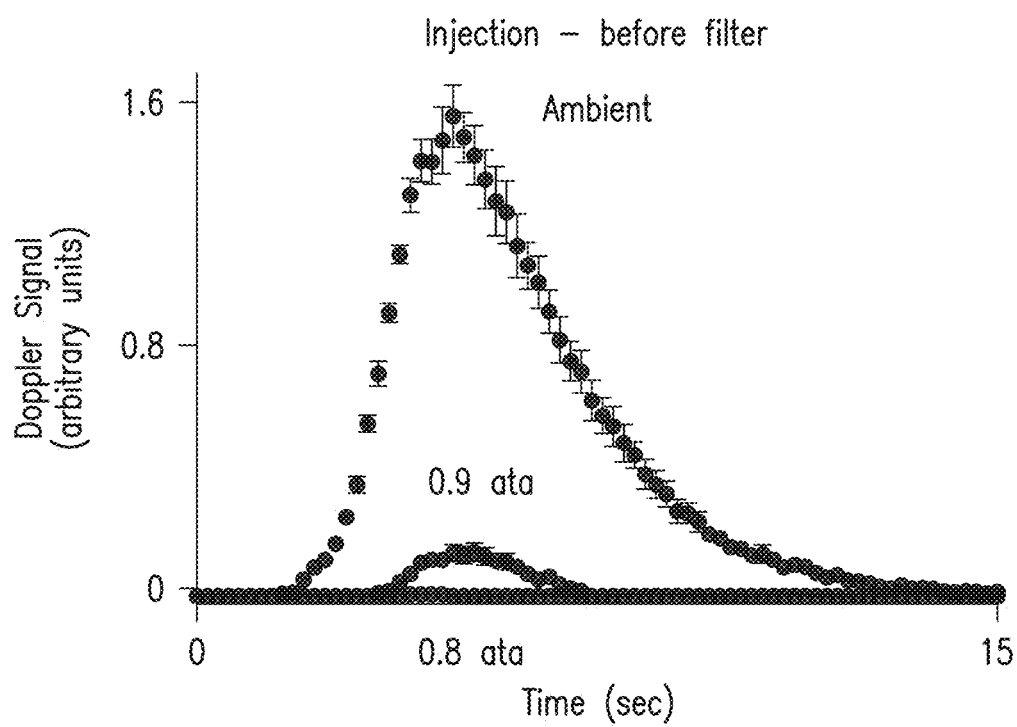
FIG. 2B is a chart of doppler signal (arbitrary units) versus time (seconds) illustrating the relationship between doppler signal and time when sweep gas pressure is varied.

FIG. 2B is a chart illustrating the relationship and effectiveness of subatmospheric sweep gas. A tiny (~20 µl) air bubble agitated by hand in 10 ml blood (using two 12 ml syringes and a 3-way stopcock) was injected upstream of the oxygenator. The emboli traversed the oxygenator and were detected proximal to the arterial filter. Application of slightly subatmospheric sweep gas pressures strongly attenuated the GME Doppler signal. Data are averages of 9-10 trials per condition.

Figure 2C:
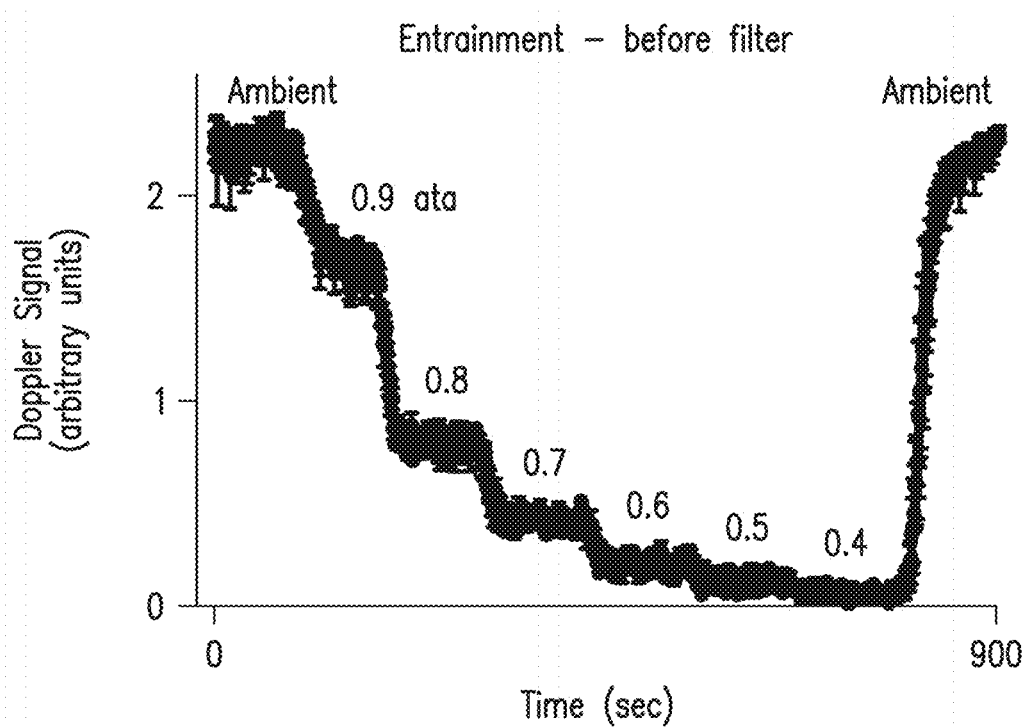
FIG. 2C is a chart of doppler signal (arbitrary units) versus time (seconds) illustrating the relationship between doppler signal and time upstream of the arterial filter when sweep gas pressure is varied.
Figure 2D:
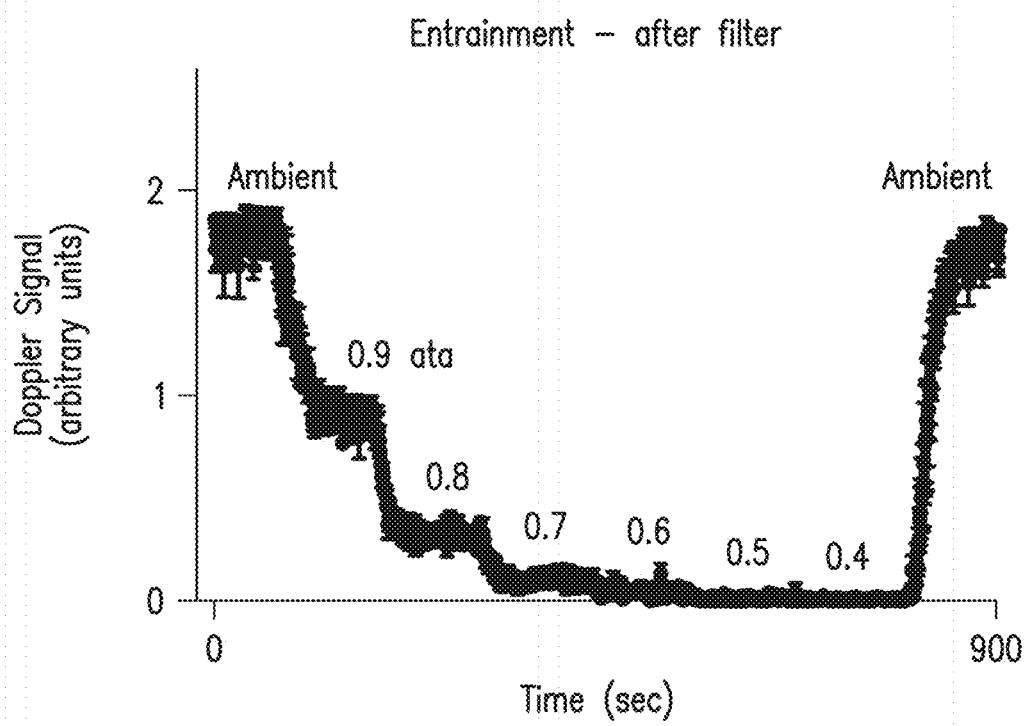
FIG. 2D is a chart of doppler signal (arbitrary units) versus time (seconds) illustrating the relationship between doppler signal and time downstream of the arterial filter when sweep gas pressure is varied.

FIGS. 2C and 2D further illustrate the relationship and effectiveness of subatmosphereic sweep gas before and after the arterial filter. Continuous entrainment of air (500 ml/minute, via luer connector) into the venous line at the reservoir entrance simulated a large, continuous embolic challenge. With ambient sweep gas pressures, strong Doppler signals were observed upstream and downstream of the arterial filter. Hypobaric oxygenation produced a robust dose-dependent reduction of the Doppler signal in both locations. Data are averages of 3 continuous trials that employed 2-minute steps to each listed pressure level.

Figure 3A:
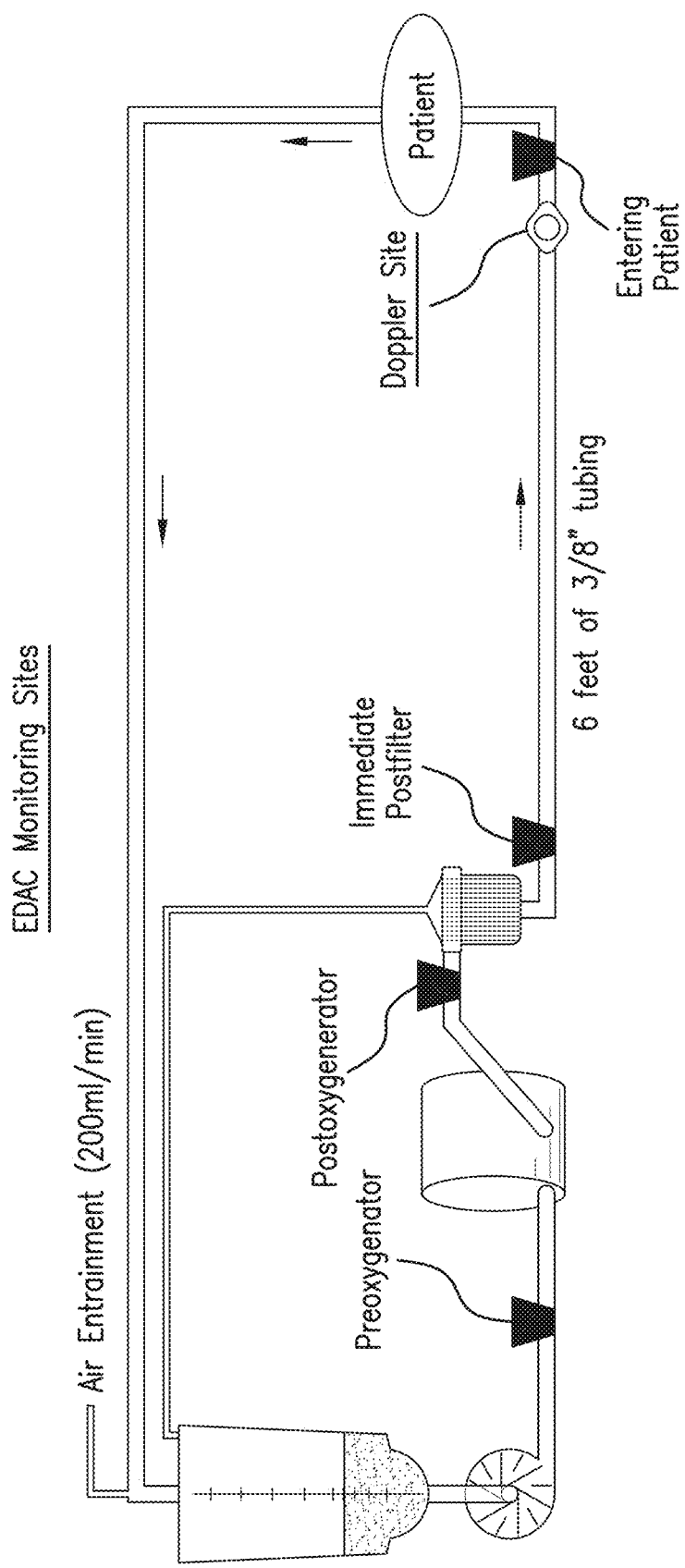
FIG. 3A is a schematic representation of an embodiment of a CPB circuit with Emboli Detection and Classification (EDAC) and Doppler monitors.
Figure 3B:
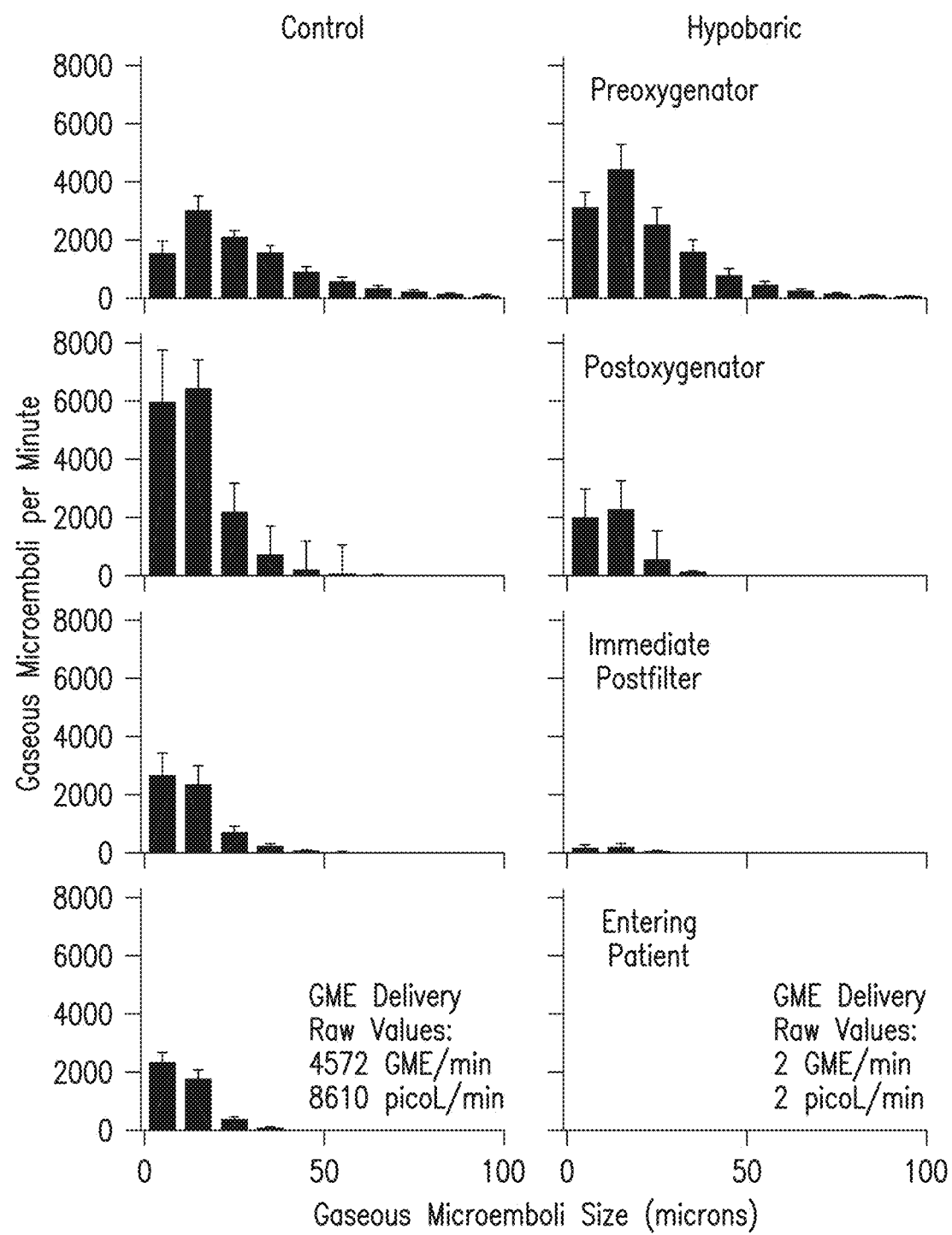
FIG. 3B is a series of histograms of gaseous microemboli per minute versus gaseous microemboli size (micrometers) showing EDAC GME counts.

FIGS. 3A and 3B relate to hypobaric oxygenation in vivo. Specifically, hypobaric oxygenation nearly eliminates GME delivery in vivo. FIG. 3A illustrates a CPB circuit with EDAC and Doppler monitors and venous air entrainment site (200 ml/minute).

FIG. 3B shows histograms showing EDAC GME counts and sizes at the four monitoring sites for both control ($O_2$/air sweep gas at ambient pressure) and hypobaric ($O_2$ sweep gas at subatmospheric pressure) conditions. Under control conditions 4500 GME/minute were delivered to the patient. Under hypobaric conditions, GME counts and volumes were similar to control at the preoxygenator location, but were progressively eliminated as they traversed the CPB circuit, reducing GME delivery to only 2/minute during this large embolic load.

FIGS. 4A-4D relate to animals managed with hypobaric oxygenation. Specifically, animals managed with hypobaric oxygenation display reduced microvascular injury in cerebral white matter.

Figure 4A:
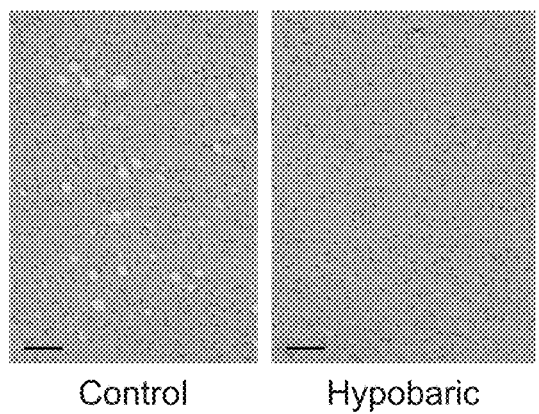
FIG. 4A is a 10× photomicrograph of 4 μm-thick hematoxylin-eosin.

FIG. 4A shows 10× photomicrographs of 4 μm-thick hematoxylin-eosin stained sections of periventricular white matter. Dilated capillaries appear as voids (white) surrounded by a single layer of endothelial cells. Scale bars=100 μm.

Figure 4B:
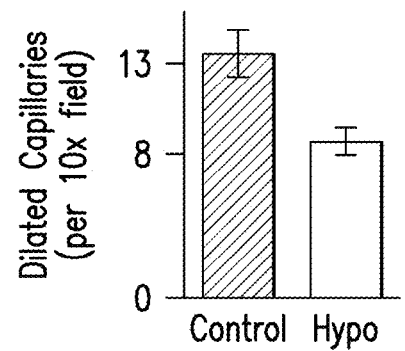
FIG. 4B is a chart of dilated capillaries illustrating the relationship between dilated capillaries and hypobaric oxygenation.
Figure 4C:
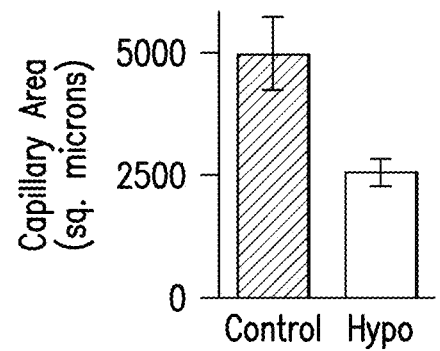
FIG. 4C is a chart of capillary area (square micrometers) illustrating the relationship between capillary area and hypobaric oxygenation.

FIGS. 4B and 4C illustrate that dilated capillaries were fewer in number and in area in animals managed using hypobaric oxygenation (control n=30 10×-fields, N=3 animals; hypobaric n=51 fields, N=5 animals; *=p<0.001).

Figure 4D:
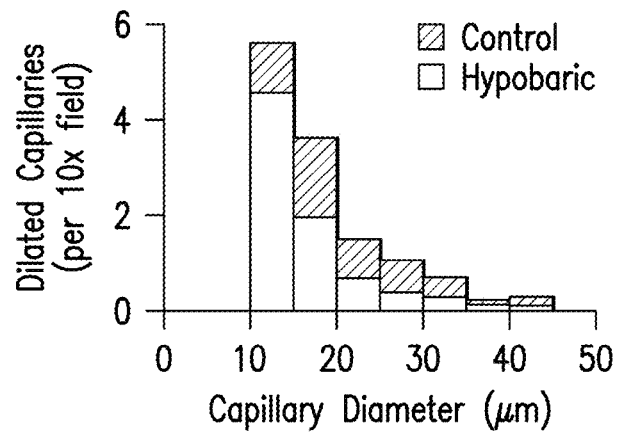
FIG. 4D is a chart of dilated capillaries versus capillary diameter (micrometers, μm) illustrating the relationship between dilated capillaries and hypobaric oxygenation with respect to capillary diameter.

Further, FIG. 4D illustrates that the difference in numbers of dilated capillaries between conditions was present at all sizes studied, to ensure that the result is not an artifact of the measurement criteria.

Figure 6:
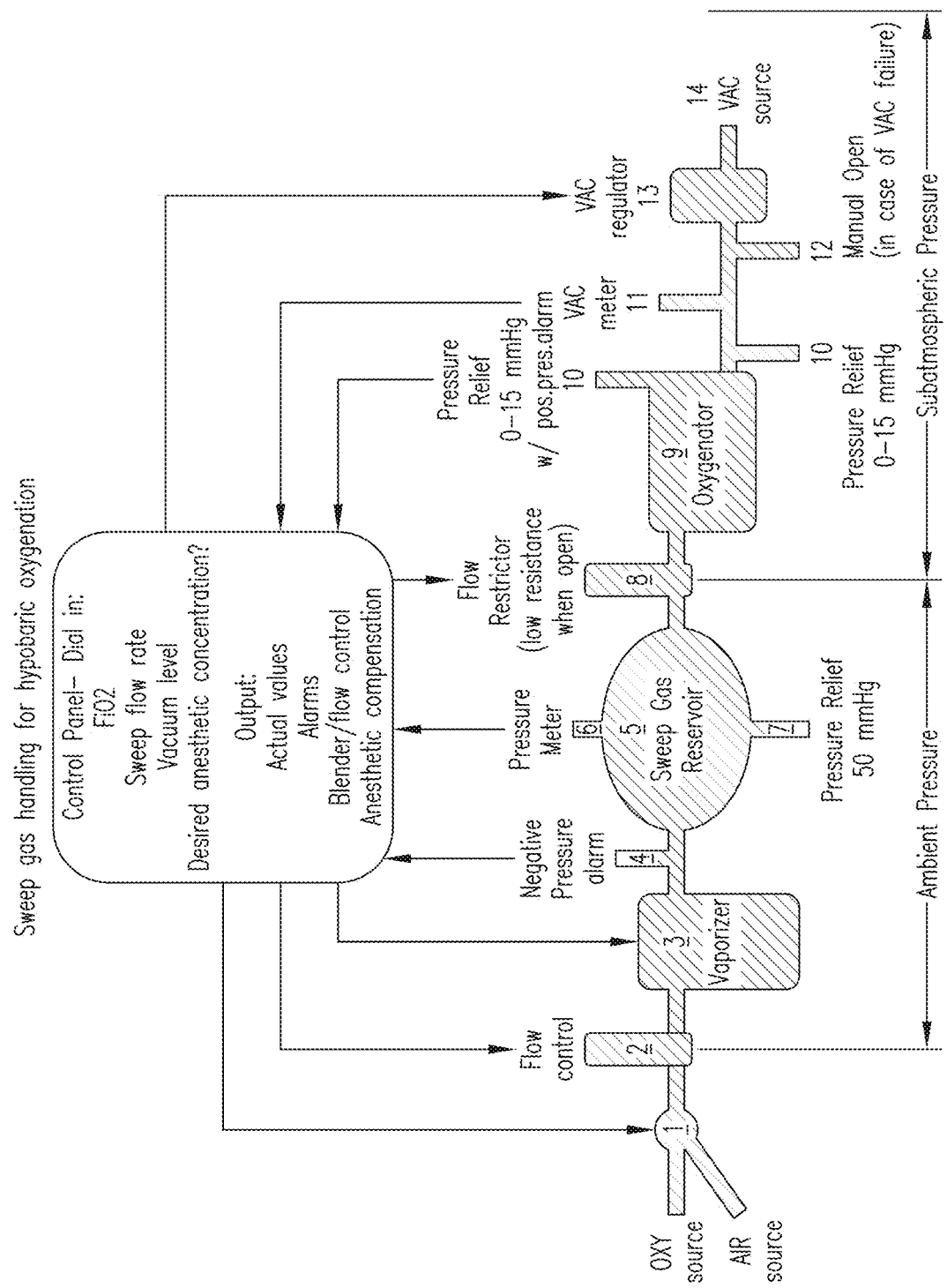
FIG. 6 is a schematic representation of a hypobaric oxygenation method in accordance with an exemplary embodiment.

FIG. 6 refers to a schematic illustration of an alternative embodiment of the CPB system. Oxygen and/or air may be introduced at inlet comprising a gas blender 1 from an oxygen source equipped with a pressure regulator configured to control a pressure of the supplied oxygen, e.g., to control the volume fraction of inspired oxygen ($F_iO_2$), and wherein a flow is controlled by flow control 2. The flow control can be a needle-valve flow controller, for example. Vaporizer 3, negative pressure alarm 4, sweep gas reservoir 5, pressure meter 6, and pressure relief 7 all operate at or near ambient pressure. Pressure relief 7 may be configured to relieve pressure in the sweep gas reservoir 5 if pressure exceeds 50 mmHg. Sweep gas reservoir 5 stores the sweep gas to be used in the oxygenation process at ambient pressure. The sweep gas reservoir 5 may be elastic. Flow restrictor 8 limits the flow of sweep gas (oxygen) into the oxygenator 9. Oxygenator 9 experiences low pressure due to vacuum imparted by vacuum source 14. Vacuum source 14 is regulated by vacuum regulator 13, and is measured by vacuum meter 11. In case of failure, manual open valve 12 may be utilized. Positive pressure relief 10 and positive pressure alarm may be utilized if subatmospheric pressure is not obtained. Pressure relief 10 may relieve pressure if pressure exceeds a given range of 0-15 mmHg. Flow restrictor 8, oxygenator 9, pressure relief 10, vacuum meter 11, manual open 12, vacuum regulator 13, and vacuum source 14 are held at subatmospheric pressure.

Additionally, a control panel may be used to control $F_iO_2$, sweep flow rate, vacuum level and the desired anesthetic concentration. Further, the control panel can output actual values, alarms, blender/flow control and anesthetic compensation. Sweep flow rate may open flow control 2 to a desired flow rate, and then adjust the flow restrictor 8 to maintain constant pressure in the sweep gas reservoir 5. Preferably, this pressure may be slightly above atmospheric, in at least one embodiment, may be 20 mmHg. The control panel may monitor the pressure meter 6. The control panel may adjust the vacuum level by monitoring the vacuum meter 11 and adjusting the vacuum regulator 13 accordingly.

Further, the desired anesthetic concentration in the system may be controlled, with various modes of operation and control methods. Several methods are contemplated herein; however the desired anesthetic concentration may be achieved by any suitable method. First, the adjustment may be made by indexing the vaporizer knob on vaporizer 3 for an assortment of vacuum levels, wherein the perfusionist adjusts the levels appropriately. Secondly, the adjustment may be made based the reading of vacuum meter 11, therefore adjusting the vaporizer 3 bypass ratio. Thirdly, the sweep gas reservoir 5 and vaporizer 3 may be exposed to subatmospheric pressures to increase vaporizer output, wherein the subatmospheric pressure may be adjusted based on the reading of vacuum meter 11. Lastly, the vaporizer may be set to a certain predetermined output, ranging preferably, but no limited to 4-8%, wherein output is mixed with a fresh $O_2$ source between the vaporizer 3 and the sweep gas reservoir 5.

EXAMPLES

Eight juvenile swine were studied. Anesthetic induction employed intramuscular acepromazine (1.1 mg/kg), glycopyrrolate (0.01 mg/kg), and ketamine (33 mg/kg), followed by 3% isoflurane inhalation with electrocardiography and pulse oximetry. Fentanyl (50 mcg in 5 ml normal saline) was administered into the lumbar cerebrospinal fluid via 20-gauge multiorifice catheter. Tracheal intubation and ear vein cannulation were followed by isoflurane maintenance in 70% $O_2$/30% $N_2$ and 50 mcg of additional spinal fentanyl when warranted by hemodynamics. After median sternotomy, a central arterial pressure catheter was placed and heparin was administered IV to achieve and maintain ACT>350 seconds (Hemochron Response, International Technidyne Corporation, Edison, N.J.). A 20-french aortic and 28-30-french bicaval CPB cannulae (Medtronic Incorporated, Minneapolis, Minn.) were placed.

Animals were assigned a priori to control or hypobaric oxygenation using a single-oxygenator, filtered CPB circuit (FIG. 3A). M3 Detector (Spectrum Medical, Cheltenham, UK) continuously monitored flow rates and arterial/venous $O_2$ saturations ($SaO_2$/$SvO_2$). $PaO_2$ was adjusted (target=200 mmHg) by varying the sweep gas oxygen/air mixture (control conditions, N=3 animals) or by applying variable subatmospheric pressure to 100% $O_2$ sweep gas (hypobaric oxygenation, N=5 animals). $PaCO_2$ (target=45 mmHg) was adjusted by varying the sweep gas flow rate in each condition. In the hypobaric condition, the predicted partial pressure of isoflurane was maintained by increasing the vaporizer dial setting to equal the desired concentration/sweep gas pressure (e.g. if 1% isoflurane were used at ambient pressure, the setting would need to be increased to 1.5% at 0.66 atmospheres absolute (ata) and to 2% at 0.5 ata to achieve an equal hypnotic effect). CPB flow rates were adjusted to maintain $SvO_2$>60%, and intermittent phenylephrine maintained arterial pressure (MAP)>50 mmHg. Reservoir volume was 250-500 ml. To conserve the animals' low starting hematocrit, mediastinal shed blood was returned to the reservoir's cardiotomy section via ¼-inch roller pump circuit. Vacuum-assisted venous drainage was used (−10 mmHg). Passive cooling was allowed to 34° C.

Air was continuously entrained throughout the CPB run (200 ml/minute, via luer connector in venous line at reservoir entrance, FIG. 3A). Single-site Doppler monitored GME semi-quantitatively in all 8 experiments. Terumo's FDA-approved Emboli Detection and Classification (EDAC) was available in 6 of 8 experiments for simultaneous 3-site ultrasound backscatter GME quantification: at preoxygenator, immediately postfilter, and either postoxygenator (N=3 animals) or 6 feet postfilter (N=3) locations. GME data were acquired in trials of 10-120 minutes duration separated by a change in CPB conditions (e.g. flow rate, reservoir volume, sweep gas composition or pressure). Brief trials of hypobaric oxygenation were performed in 2 of 3 animals otherwise managed with control conditions. Thus, hypobaric data are from N=7/8 animals for Doppler and N=5/6 animals for EDAC, while all control data are from N=3 animals (number of trials (n) listed in Results). As CPB parameters are likely larger determinants of microembolization than the animal downstream of the CPB circuit, GME data trials were considered to be independent observations for statistical analysis.

Hematologic samples taken before CPB, then after two and four hours of CPB, were analyzed for RBC morphology and plasma hemoglobin. End organs were fixed with neutral buffered formalin (10%, 3 liters, 5 minutes) via CPB circuit before harvest.

Paraffin-embedded, 4 µm hematoxylin-eosin sections from the frontal lobe, thalamus, caudal lobe, mesencephalon, cerebellum, medulla, and renal cortex were evaluated microscopically by veterinary pathologists for cytoarchitectural integrity. Then, blinded quantification of dilated capillaries (>10 µm diameter) was performed in white matter adjacent to the lateral ventricle and subependymal zone (periventricular white matter, ~10 10× fields per animal). Due to the expected heterogeneous nature of tissue effects and the exploratory nature of the post-hoc microvascular analysis, we treated each field as an independent data point with respect to microvascular injury.

Data are presented as mean±SEM. Continuous variables were compared using two-tailed Student's t-tests (significance at $P<0.05$). A linear fit was performed using Prism (GraphPad Software, La Jolla, Calif.). Dose-dependence was assessed using Spearman's Rank Correlation Coefficient. GME data trials and tissue specimens were treated as independent observations for statistical analyses.

In vitro Gas Exchange: Reduction of Dissolved Gases in Blood

TABLE 1

In vitro Gas Exchange

|  | $O_2$ Tension (mmHg) | $CO_2$ tension (mmHg) | # of trials |
|---|---|---|---|
| Arterial Blood Gases |  |  |  |
| Ambient sweep gas pressure | 527 ± 12 | 44.6 ± 4.9 | 3 |
| 0.8 ata | 359 ± 7 | 40.2 ± 2.3 | 3 |
| 0.6 ata | 205 ± 6 | 42.0 ± 4.2 | 3 |
| 0.4 ata | 96 ± 4 | 30.3 ± 2.3 | 3 |
| Venous Blood Gases |  |  |  |
| Ambient sweep gas pressure | 63.0 ± 3.8 | 52.4 ± 5.5 | 3 |
| 0.8 ata | 61.3 ± 2.3 | 48.0 ± 3.8 | 3 |
| 0.6 ata | 61.0 ± 2.0 | 56.3 ± 6.0 | 3 |
| 0.4 ata | 59.3 ± 0.3 | 52.7 ± 2.4 | 3 |

Hypobaric oxygenation (FIG. 1A) was used with a simulated patient on CPB (FIG. 1B) to assess the effect of subatmospheric sweep gas pressures on oxygenation and $CO_2$ removal from blood in the absence of nitrogen. As expected, lowering the pressure of pure oxygen sweep gas decreased $PaO_2$ in a smooth, linear manner (Table 1, FIG. 1C, $R^2$=0.99). In contrast, $PaCO_2$ was largely stable with decreasing sweep gas pressures, with possibly increased efficiency of $CO_2$ removal at the lowest pressures applied (Table 1, FIG. 1D). Indeed, $CO_2$ removal was easily managed independently of oxygenation by adjusting the sweep gas flow rate in experiments. Hypobaric oxygenation was confirmed to reduce dissolved nitrogen in blood by 85.4±0.7% using mass spectroscopy (n=3 trials, p<0.001, denitrogenation likely underestimated, see supplemental information). No detrimental effects on the oxygenator or gas exchange were observed in any experiments. During simulated vacuum failure, the positive-pressure relief valve successfully prevented air embolism (data not shown). Together, these data indicate that hypobaric oxygenation is a reliable, efficient method for managing gas exchange during CPB that reduces the sum of partial pressures of dissolved gases to subatmospheric levels.

In Vitro GME: Dose-Dependent Removal

Next tested was whether hypobaric oxygenation improves GME removal in the CPB circuit. First, GME boluses were injected upstream of the oxygenator (FIG. 2A). When the oxygenator used 100% oxygen sweep gas at ambient pressure, a robust downstream Doppler signal was observed (FIG. 2B). Modest reduction of sweep gas pressure to 0.9 ata reduced the Doppler signal by 94.8±1.0% from control (area under curve, range 90.9-98.3%, n=9 trials, p<0.001), while at 0.8 ata the signal was barely discernible (reduced 99.6±0.07% from control, range 99.3-99.8%, n=10 trials, p<0.001). Next, air entrainment simulated a large ongoing embolic load. Reductions in sweep gas pressure again produced a robust dose-dependent reduction of the Doppler signal measured before the arterial filter (FIG. 2C, reduced by 26±3% when the sweep gas pressure was 0.9 ata, 66±2% at 0.8 ata, 83±2% at 0.7 ata, 91±0.2% at 0.6 ata, 95±2% at 0.5 ata, and 98±1% at 0.4 ata, Spearman's rank correlation coefficient ρ=1.0, n=3 continuous trials). When the Doppler was moved downstream of the arterial filter, a substantial embolic signal persisted under normobaric conditions despite the use of arterial filtration (81±3% of pre-filter baseline signal, FIG. 2D). The downstream signal was reduced even more effectively by reductions in sweep gas pressure (by 53±4% of post-filter baseline at 0.9 ata, 83±2% at 0.8 ata, 94±1% at 0.7 ata, 99±0.3% at 0.6 ata, 99.5±0.1% at 0.5 ata, and 99.7±0.1% at 0.4 ata, p=1.0, n=3 continuous trials). Together, these data demonstrate that the use of hypobaric oxygenation improves the ability of the CPB circuit to remove GME from circulating blood in a dose-dependent fashion.

Swine CPB: Safe Maintenance of Large Animals

TABLE 2

Swine Characteristics

|  | Control | Hypobaric | P value |
|---|---|---|---|
| Swine Characteristics |  |  |  |
| Gender | 2M/1F | 4M/1F |  |
| Mass (kg) | 43.5 ± 1.8 | 42.3 ± 1.5 | 0.64 |
| Hematocrit$_{start}$ (%) | 21.3 ± 1.2 | 22.2 ± 1.0 | 0.61 |
| Hematocrit$_{end}$ (%) | 18.3 ± 0.3 | 18.8 ± 0.4 | 0.43 |
| Induction to CPB (minutes) | 168 ± 10 | 176 ± 8 | 0.58 |
| Blood Gases |  |  |  |
| pH | 7.30 ± 0.06 | 7.40 ± 0.01 | 0.06 |
| $P_aCO_2$ (mmHg) | 52.1 ± 2.0 | 45.0 ± 1.3 | 0.02 |
| $P_aO_2$ (mmHg) | 190 ± 14 | 184 ± 14 | 0.81 |

TABLE 2-continued

Swine Characteristics

|  | Control | Hypobaric | P value |
|---|---|---|---|
| $S_aO_2$ (%) | 99.6 ± 0.4 | 99.6 ± 0.2 | 0.91 |
| $S_vO_2$ (%) | 66.2 ± 1.0 | 66.7 ± 2.4 | 0.88 |
| Bypass Parameters | | | |
| Sweep pressure (ata) | 1 (ambient) | 0.66 ± 0.03 | |
| Sweep $F_iO_2$ (%) | 0.68 ± 0.02 | 1.0 | |
| MAP (mmHg) | 51.0 ± 1.6 | 52.2 ± 1.8 | 0.68 |
| Flow Rate (liters/minute) | 4.25 ± 0.14 | 4.04 ± 0.21 | 0.36 |
| Pump Time (hours) | 4.57 ± 0.23 | 4.52 ± 0.14 | 0.86 |

CPB in 40 kg swine using hypobaric oxygenation was characterized by stable, easily adjustable gas exchange parameters with no adverse effects noted in the animal, oxygenator, or CPB circuit. Animal characteristics and CPB management data are listed in Table 2. Notably, lowering the partial pressure of oxygen in the sweep gas using dilution with nitrogen ($F_iO_2$=68.3±1.7% in control) or using vacuum (pressure=0.66±0.03 ata in hypobaric conditions) produced similar $PaO_2$ values, suggesting that hypobaric oxygenation preserves oxygenator gas exchange efficiency. A small increase in $CO_2$ tension in control animals was due to a slightly lower sweep gas flow rate in the absence of vacuum. Overall, hypobaric oxygenation was a reliable, practical method for maintaining large animals during CPB.

Swine GME: Progressive Elimination in the CPB Circuit

During continuous air entrainment, single-site semi-quantitative Doppler and multisite quantitative EDAC detected GME in the CPB circuit (FIG. 3A). Data were collected in discrete trials (n) separated by a change in CPB parameters in N=8 total swine. Hypobaric oxygenation reduced the Doppler signal near the aortic cannula by 99.1±0.3% (range 95.8-100%, n=16 trials, N=7 swine) compared with control (n=7, N=3). EDAC data from hypobaric (N=5 swine) and control (N=3) conditions are presented in FIG. 3B. Proximal to the oxygenator, EDAC GME counts and volumes were similar between hypobaric (n=10 trials, p>0.29) and control (n=7). Downstream from the oxygenator, GME numbers in the hypobaric condition were greatly reduced compared with controls: at the post-oxygenator location by 68.4±14.1% (range 13.1-91.3%, n=5, p<0.05), at the post-arterial filter location by 92.6±4.2% (range 57.8-99.8%, n=10, p<0.01), and at the entering patient location by 99.96±0.02% (range 99.87-99.99%, n=5, p<0.001). GME volumes were also reduced at the post-oxygenator location by 80.5±5.6% (range 62.2-95.6%, n=5, p<0.05), at the post-filter location by 94.9±2.9% (range 74.3-99.8%, n=10, p<0.01), and at the entering patient location by 99.97±0.01% (range 99.94-100%, n=5, p<0.001). Control trials numbered n=3, 7, and 4 in these respective locations. These data demonstrate that hypobaric oxygenation strongly enhances GME removal from the CPB circuit in vivo. Further, they indicate that the site of enhanced GME removal extends progressively from the oxygenator to the arterial filter to the blood itself as it flows toward the patient. Importantly, data acquired closest to the patient show near-total elimination of GME delivery from the CPB circuit by the combined use of arterial filtration and hypobaric oxygenation, despite a large upstream embolic load.

Swine Tissue Analysis: Normal Histology with Reduced Microvascular Damage

FIGS. 5A-5D illustrate microscopic evaluation of peripheral blood, brain, and kidney from animals managed with hypobaric oxygenation (Scale bars=100 μm). Specifically, these figures revealed normal cytoarchitecture.

One skilled in the art would expect that an oxygenator using nitrogen-free sweep gas at any pressure would create a maximal gradient for $N_2$ removal, thereby denitrogenating blood that flows through it, even if the sum of partial pressures of the remaining $O_2$ and $CO_2$ in the blood totaled less than the ambient pressure. However, since the proposed mechanism for reabsorbing air bubbles into the blood phase depends critically on reducing the sum of partial pressures of dissolved gases, it was optimal to confirm experimentally that $N_2$ tension was indeed reduced during hypobaric oxygenation. As $N_2$ tension is not measured by standard blood gas analysis, mass spectrometry was utilized. The analysis employed a single oxygenator CPB circuit where $O_2$ bubbles could be injected into a flowing blood stream, then made to exchange gases with that blood, then recollected in a bubble trap and sampled. Reasonably, the dissolved $N_2$ in blood would accumulate in the $O_2$ bubbles during their passage, and would then be detected by mass spectrometry. Oxygen (20-30 ml) was agitated in blood and injected slowly into the circuit downstream of the oxygenator, where it was made to flow through the pores of an arterial filter to enhance exchange of gases with the blood, then collected in a bubble trap and sampled at ambient pressure using a 100 μl gaslock syringe (Supelco Analytical). Mass spectrometry (Agilent 5975C GC-MS) was used to analyze control samples of 100% $O_2$ and room air, then the test sample gas was introduced in volumes of 20-100 μl. The gas mixtures were injected and run through a HP-5MS column with helium gas flow controlled at 1 ml/min. The mass spectrometer ion source, column and quadrupole were maintained at 50° C. The mass spectrometer was used in the electron impact mode and the mass range for ion acquisition was 14 to 200 atomic mass units (amu). Molecular ions of $O_2$ and $N_2$ were monitored by their respective molecular ions of mass-to-charge (m/z) 32 and m/z 28. The peak ion abundances for m/z 28 ($N_2$) and m/z 32 ($O_2$) amu were measured, and an $O_2/N_2$ fraction was calculated by interpolation between the $O_2$ and air calibration samples.

Blood was oxygenated in a single-oxygenator circuit using a sweep gas mixture of 50% $O_2$/50% $N_2$ at ambient pressure to produce blood containing dissolved $N_2$. When $O_2$ bubbles were passed through this blood, then collected and analyzed they had accumulated 41.7+/−2.3% $N_2$ by mass (n=7 trials). The same blood was oxygenated with 100% $O_2$ sweep gas at 0.5 atmospheres absolute (ata) to produce a similar moderate level of oxygenation in the absence of $N_2$. $O_2$ bubbles that were passed through this blood accumulated significantly less $N_2$ (6.1+/−0.3%, n=3 trials, p<0.001). The magnitude of the denitrogenation is likely underestimated by these data, as there were several opportunities for contamination of the $O_2$ samples with room air during the processes of injection, sampling, and measurement. The data indicate a clear reduction of $N_2$ tension during hypobaric oxygenation, consistent with the proposed mechanism of GME reabsorption through reduction of the sum of partial pressures of dissolved gases in blood.

Figure 5A:
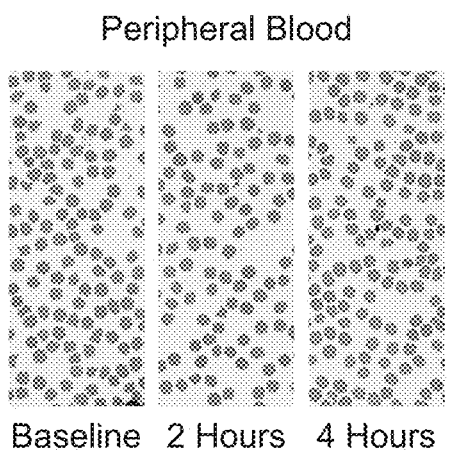
FIG. 5A are blood photomicrograph samples taken before initiation of CPB (baseline), then after two and four hours of CPB with hypobaric oxygenation.
Figure 5B:
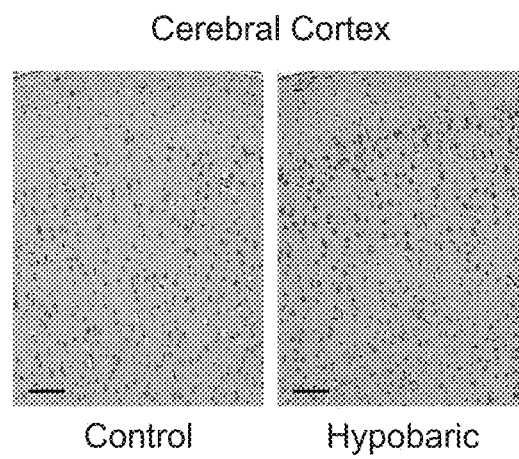
FIG. 5B are photomicrograph samples of Hematoxylin-eosin stained, paraffin-embedded, 4 μm thick sections from cerebral cortex.
Figure 5C:
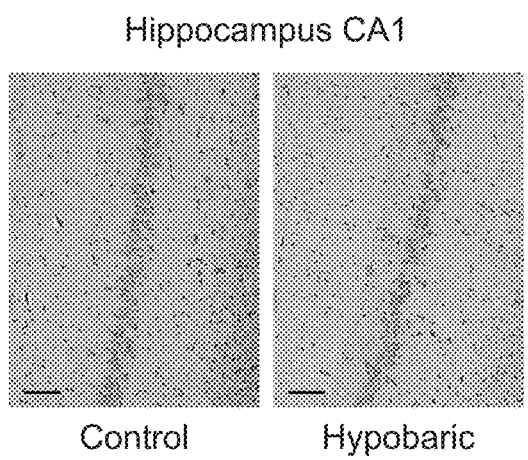
FIG. 5C are photomicrograph samples of hippocampal region CA1.
Figure 5D:
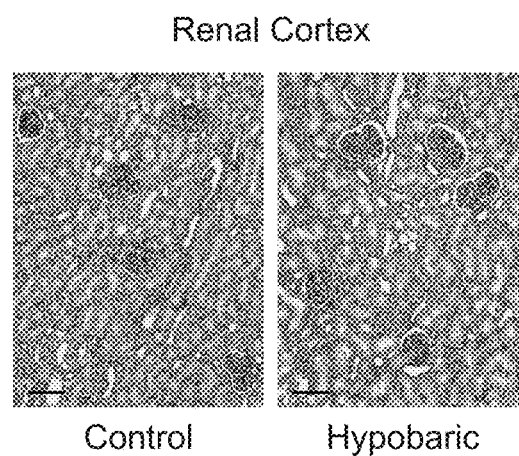
FIG. 5D are photomicrograph samples of renal cortex.

FIG. 5A illustrates peripheral blood smears were made from samples taken before initiation of CPB (baseline), then after two and four hours of CPB with hypobaric oxygenation. At 1000× magnification, smears display red blood cell echinocytes with a crenated appearance, which is typical for swine, but no evidence of cellular injury or hemolysis. FIG. 5B illustrates Hematoxylin-eosin stained, paraffin-embedded, 4 μm thick sections from cerebral cortex without apparent abnormality. FIG. 5C illustrates hippocampal region CA1 without apparent abnormality. FIG. 5D illustrates renal cortex without apparent abnormality.

Much like the human lung, hollow fiber microporous membrane oxygenators are very efficient at exchanging $O_2$ and $CO_2$ between sweep gas and blood when the sweep gas flow rate is adequate. The human lung more rapidly equilibrates the partial pressures of gases or vapors (e.g. anesthetic vapors) with lower blood solubility compared with those of greater blood solubility. Similarly, it is expected the addition or removal of $N_2$ by the oxygenator to be more efficient than the exchange of $O_2$ or $CO_2$ due to its lower solubility in blood. As known in the art, the partial pressure of $N_2$ in blood exiting the oxygenator approaches zero when the sweep gas does not contain $N_2$, a simple sum of the measured partial pressures of $O_2$ and $CO_2$ in Table 1 and the hypobaric column of Table 2 should provide reasonable estimates of the sum of partial pressures of dissolved gases in experiments. For the Control column of Table 2, the partial pressure of $N_2$ in the sweep gas would also need to be added to estimate the sum of partial pressures of dissolved gases.

Since the washout of $N_2$ from the body is somewhat prolonged due to the slowly mobilized stores of $N_2$ in fat, the swine in the experiments are expected to serve as sources of $N_2$ in the venous blood. As the measurement of dissolved $N_2$ in blood is difficult and would be impractical in a clinical situation, one skilled in the art would provide estimates of $N_2$ elimination from the swine. Anesthetized patients before CPB initiation are frequently exposed to inspired $O_2$ in the 60-100% range, and thus are partially denitrogenated before CPB. Based on a published human denitrogenation time course, one skilled in the art would estimate that the swine have 60% equilibrated to the 70% $O_2$/30% $N_2$ ventilator gas during the 176+/−8 minutes from anesthetic induction to initiation of CPB in our hypobaric experiments. Using this estimate to modify a published 4-hour $N_2$ elimination time course from 37-kg swine previously equilibrated to air breathing, it is estimated the $N_2$ elimination from a 42.3-kg swine to be 4.8 ml/minute during the first 7 minutes of CPB using $N_2$-free sweep gas, 1.9 ml/minute at 1 hour, and 0.5 ml/minute at 4 hours. Using the published $N_2$ solubility in human blood at body temperature of 1.27 ml $N_2$ per 100 ml blood and the mean CPB flow rate of 4 liters/minute, the eliminated nitrogen accounts for a venous partial pressure of dissolved $N_2$ from the animal of 68 mmHg during the first 7 minutes, 23 mmHg at 1 hour, and 8 mmHg at 4 hours of CPB.

As the cylindrical hollow fiber microporous oxygenator membranes are not expected to transfer pressures from the sweep gas compartment into the blood phase, it is not expected for blood cells to experience hypobaric pressures. Indeed, subatmospheric sweep gas pressures did not affect arterial line blood pressures at the oxygenator outlet (differences from control ranged from −0.8 to +0.6 mmHg at 0.5 ata (n=14 trials, p>0.9) and from −0.6 to +0.5 mmHg at 0.1 ata (n=14 trials, p>0.4). Additionally, no plasma hemoglobin or morphologic evidence of hemolysis was observed in blood samples taken before and during hypobaric oxygenation in swine (FIG. 5A).

Experienced veterinary pathologists generally found no cytoarchitectural abnormality or apparent difference between animals in fixed postmortem tissue from six brain regions and the renal cortex (FIGS. 5B-5D). However, the presence of abnormal dilated capillaries in some white matter regions was noted. Since small capillary and arteriolar dilations are known responses to microembolization. Blinded post-hoc analysis in periventricular white matter revealed that reduction of GME during hypobaric oxygenation was accompanied by 35.8±5.5% and 48.7±5.7% reductions in the number and area of dilated capillaries, respectively (FIG. 4, p<0.001) when compared with control. Similar findings were observed at all capillary diameters studied (FIG. 4D). Collectively, these data suggest that elimination of GME is accompanied by reduced microvascular injury in animals maintained using hypobaric oxygenation.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Exemplary embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A system for cardiopulmonary bypass, the system comprising:
   an oxygen source comprising a pressure regulator configured to regulate an oxygen pressure;
   an oxygenator fluidly connected to the pressure regulator of the oxygen source via a sweep gas inlet, wherein the sweep gas inlet is directly connected to the oxygenator and is configured to have a subatmospheric pressure, and the oxygenator is configured to oxygenate blood;
   a vacuum regulator fluidly connected to the oxygenator via a sweep gas outlet, and configured to provide the subatmospheric pressure; and
   a flow restrictor directly connected to the sweep gas inlet and configured to provide a pressure drop from the oxygen source to the oxygenator.

2. The system of claim 1, further comprising a positive pressure relief valve fluidly connected to the sweep gas outlet.

3. The system of claim 1, wherein the oxygenator is a membrane oxygenator having a sealed housing.

4. The system of claim 1, further comprising an arterial filter fluidly connected to a blood outlet of the oxygenator.

5. The system of claim 4, further comprising a first Doppler site in fluid communication with the blood outlet of the oxygenator and a second Doppler site in fluid communication with an outlet of the arterial filter.

6. The system of claim 1, further comprising an air inlet in fluid communication with the sweep gas inlet.

7. The system of claim 1, further comprising a vaporizer in fluid communication with the flow restrictor.

8. The system of claim 1, further comprising an arterial filter in fluid communication with a blood outlet of the oxygenator.

9. A system for cardiopulmonary bypass, the system comprising:
- an oxygen source comprising a pressure regulator configured to regulate an oxygen pressure;
- a flow control configured to receive the oxygen source;
- an oxygenator fluidly connected to the flow control via a sweep gas inlet, wherein the sweep gas inlet is directly connected to the oxygenator and is configured to have a subatmospheric pressure, and the oxygenator is configured oxygenate a blood;
- a vacuum regulator fluidly connected to the oxygenator via a sweep gas outlet, and configured to provide the subatmospheric pressure; and
- a flow restrictor directly connected to the sweep gas inlet and configured to provide a pressure drop from the oxygen source to the oxygenator.

10. The system of claim 9, further comprising a vaporizer in fluid communication with the flow control.

11. The system of claim 10, wherein the vaporizer is configured to operate at atmospheric pressure.

12. The system of claim 9, wherein the oxygenator is a membrane oxygenator with a sealed housing.

13. The system of claim 9, further comprising a control panel configured to operatively control parameters of at least one system component.

14. The system of claim 9, further comprising a cardiopulmonary bypass reservoir;
- a pump in fluid communication with the cardiopulmonary bypass reservoir configured to provide pressure to the system;
- an arterial filter fluidly connected to a blood outlet of the oxygenator and to the cardiopulmonary bypass reservoir; and
- a patient interface fluidly connected to the arterial filter and to the cardiopulmonary bypass reservoir.

15. A method to oxygenate blood for cardiopulmonary bypass, the method comprising:
- providing a subatmospheric pressure in a membrane oxygenator with a sealed housing via a vacuum regulator;
- introducing subatmospheric pressure oxygen to the membrane oxygenator via a pressure regulator and a flow restrictor; and
- introducing blood to be oxygenated to the subatmospheric pressure oxygen to oxygenate the blood,
- wherein the subatmospheric pressure oxygen flows from the flow restrictor directly to a sweep gas inlet and through the sweep gas inlet directly to the membrane oxygenator.

16. The method of claim 15, further comprising storing blood to be oxygenated in a cardiopulmonary bypass reservoir.

17. The method of claim 15, further comprising filtering oxygenated blood in an arterial filter.

18. The method of claim 15, further comprising delivering oxygenated blood to a patient.

19. The method of claim 15, further comprising receiving blood to be oxygenated in a cardiopulmonary bypass reservoir.

20. The method of claim 15, further comprising monitoring gaseous microemboli via an emboli detection site.

21. The method of claim 15, further comprising introducing an anesthetic vapor into a sweep gas at ambient pressure via a vaporizer.

* * * * *